United States Patent [19]

Au et al.

[11] Patent Number: 5,401,839
[45] Date of Patent: Mar. 28, 1995

[54] PROCESS OF PREPARING N-SUBSTITUTED ALDONAMIDES HAVING IMPROVED COLOR AND COLOR STABILITY

[75] Inventors: Van Au, Peekskill, N.Y.; Bijan Harirchian, South Orange, N.J.

[73] Assignee: Lever Brothers Company, Division of Conopco, Inc., New York, N.Y.

[21] Appl. No.: 35,853

[22] Filed: Mar. 23, 1993

[51] Int. Cl.$^6$ ............... C07H 15/00; C07H 15/04; C07G 3/00; C07C 235/06
[52] U.S. Cl. .................... 536/18.7; 514/53; 536/1.11; 536/4.1; 536/18.5; 536/17.2; 536/22.1; 536/124; 536/123.13
[58] Field of Search ............. 536/18.7, 1.11, 4.1, 536/22.1, 124, 18.5, 17.2; 514/53

[56] References Cited

U.S. PATENT DOCUMENTS

| | | | |
|---|---|---|---|
| 2,662,073 | 12/1953 | Mehltretter et al. | 514/53 |
| 2,746,916 | 5/1956 | Magariello | 514/53 |
| 2,752,334 | 6/1956 | Walton | 514/53 |
| 4,741,854 | 5/1988 | Krupa et al. | 252/188.21 |
| 4,774,231 | 9/1988 | Petitou et al. | 514/53 |
| 5,037,973 | 8/1991 | Meinetsberger | 536/1.11 |
| 5,296,588 | 3/1994 | Au et al. | 536/1.11 |
| 5,336,765 | 8/1994 | Au et al. | 536/18.5 |

FOREIGN PATENT DOCUMENTS

2227008 11/1974 France .

OTHER PUBLICATIONS

Chemical Abstracts, vol. 82, No. 19, May 12, 1975, abstract 82:125563k.
Kobayashi, Kazukiyo, et al. "Synthesis and Functions of Polystyrene Derivatives Having Pendant Oligosaccharides". Polymer Journal, vol. 17, No. 4, (1985), pp. 567–575.
Williams, Taffy J., et al. "A New Class of Model Glycolipids: Synthesis, Characterization, and Interaction with Lectins." Archives of Biochemistry and Biophysics, vol. 195, No. 1, (Jun. 1979). pp. 145–151.
Ziegast, Gerd et al., "Coupling of mono- and oligosaccharides to α,w-diamino substituted poly(oxyethylene) and multifunctional amines by amide linkage", Makromol. Chem., Rapid Commun. vol. 5, (1984), pp. 373–379.
Chemical Abstract of CA 113(9):76738U. Aug. 27, 1990.
Chemical Abstract of CA 77(7):47104S. Aug. 14, 1972.
Song, Pill-Soon et al. "Kinetic Behavior and Mechanism of Inhibition of the Maillard Reaction. III. Kinetic Behavior of the Inhibition in the Reaction Between D-Glucose and Glycine." Journal of Food Science, vol. 32, (1967), pp. 98–106.
European Search Report, EP92204033, 19 Apr. 1993.
Taravel, Francois R. "Amphiphilic properties of synthetic glycolipids based on amide linkages, 4". Makromol. Chem., vol. 191 (1990), pp. 3097–3106.
Ullmann's Encyclopedia of Industrial Chemistry, vol. A14: Immobilized Biocatalysts to Isoprene, (1989), pp. 448–449.
Abstract of JP 3034946. Patent Abstracts of Japan, 14 Feb. 1991, abstract 015163.

*Primary Examiner*—Ronald W. Griffin
*Attorney, Agent, or Firm*—Rimma Mitelman

[57] ABSTRACT

A process of preparing N-substituted aldonamides, the process including the steps of mixing and reacting an aldonolactone and an amine in an organic polar solvent, in the presence of an antioxidant and a reducing agent. The aldonamides have improved color; the discoloration or browning of the aldonamides upon storage or elevated temperature processing is eliminated or substantially minimized.

21 Claims, No Drawings

PROCESS OF PREPARING N-SUBSTITUTED ALDONAMIDES HAVING IMPROVED COLOR AND COLOR STABILITY

FIELD OF THE INVENTION

The invention relates to an improved process of preparing N-substituted aldonamides.

RELATED ART

An aldonamide is defined as the amide of an aldonic acid and an aldonic acid in turn is defined as a sugar substance (e.g., any cyclic sugar) in which the aldehyde group (generally found at the $C_1$ position on the sugar) has been replaced by a carboxylic acid. Aldonamides may be based on compounds comprising one saccharide unit (e.g., gluconamide), two saccharide units (in which case aldonamides are termed aldobionamides, e.g., lactobionamide or maltobionamide) or they may be based on compounds comprising more than two saccharide units, as long as the polysaccharide has a terminal sugar unit with an aldehyde group available for oxidation.

Walton et al. (U.S. Pat. No. 2,752,334) discloses a process for the preparation of the N-substituted lactobionamides by reacting the corresponding organic primary or secondary amine with lactobiono-1,5-lactone. The reaction is effected by heating the reactants with a solvent in the case of the amines having a higher boiling point. However, the use of a solvent and lower temperature is said to give better yields with less chance of decomposition in the course of the reaction and therefore a purer product. Reaction temperatures within the range from 65° to 140° C. are said to be preferred. Yields of from 70 to 75% were reported.

Kobayashi et al., "Synthesis and Functions of Polystyrene Derivatives Having Pendant Oligosaccharides," Polymer Journal, Vol. 17, No. 4, 567-575 (1985), describe a process wherein a lactone is dissolved in refluxing methanol and a solution of amine in ethanol is added. The mixed solution is refluxed for two hours. 82% yield was reported.

Williams et al., "A new Class of Glycolipids: Synthesis, Characterization, and Interaction with Lectins," Archives of Biochemistry and Biophysics, Vol. 195. No. 1, June, 145-151, 1979, describe a process wherein a lactone was dissolved in methanol by gentle heating, an amine was added, and the reaction mixture was stirred overnight at room temperature. 70% yield was reported.

Ziegast et al., "Coupling of Mono- and Oligosaccharides to δ-w-diamino substituted Poly(oxyethylene) and Multifunctional Amines by Amide Linkage", Makromol Chem., Rapid Commun. 5, 313-379 (1984) disclose the procedure for coupling of carbohydrates to various compounds: saccharide is converted into the aldonic acid lactone via electrolytic oxidation and subsequent binding to an amino group containing carrier by amide linkage. The reaction according to Ziegast et al. requires an excess of lactone, which is subsequently separated by using relatively strong basic ion exchange column. Ziegast et al. employ an excess of lactone and conduct the reaction at 70° C. or above.

Aldonamides are carbohydrate-based molecules and, as such, represent a source of renewable raw materials that are synthetically versatile and environmentally friendly. Aldonamides have useful physical properties (e.g., surfactancy) which makes them suitable for many applications in personal care, dental, detergent and cosmetic areas. Surfactant compositions incorporating aldonamides have been described in a co-pending commonly assigned application, Ser. No. 07/981,737, incorporated by reference herein. It is possible to attain aldonamides as white crystalline solid. It has been observed, however, that at least some aldonamides included in formulations which undergo elevated temperature (i.e. up to about 85° C.) processing, e.g. personal washing bars, change color from white to brown. It is desirable to improve the color stability of aldonamides compositions containing aldonamides and undergoing elevated temperature processing.

Accordingly, it is an object of the invention to provide an improved process of manufacturing aldonamides.

It is another object of the invention to provide a process of preparing aldonamides wherein discoloration of aldonamides under subsequent elevated temperature processing is substantially minimized or eliminated. Aldonamides are attained which do not turn brown under subsequent elevated temperature processing.

These and other objects of the invention will become more apparent from the detailed description and examples that follow.

SUMMARY OF THE INVENTION

The above objects are accomplished by the present invention which includes a process of preparing an N-substituted aldonamide, the process including the steps of:

i) preparing a homogeneous mixture comprising an aldonolactone, a reducing agent, an antioxidant, an organic polar solvent, and an amine $HNR^1R^2$, wherein $R^1$ and $R^2$ are the same or different and may contain heteroatoms and are selected from the group consisting of hydrogen, an aliphatic hydrocarbon radical, an aromatic radical, a cycloaliphatic radical, an amino acid ester, an ether amine and mixtures thereof, except that $R^1$ and $R^2$ are not both hydrogen at the same time, wherein the molar ratio of the aldonolactone to the amine is in the range of from about 1.1:1 to about 1:1; and ii) reacting the homogeneous mixture at a temperature not greater than 65° C. to obtain the aldonamide.

The present invention is based in part on the discovery that the inclusion of an antioxidant and a reducing agent into the reaction mixture during the preparation of aldonamides substantially decreased or eliminated discoloration during subsequent elevated temperature processing of compositions containing aldonamides. The antioxidant and the reducing agent may be added separately or as a mixture, or the antioxidant may be added in a mixture with part of the reducing agent, and the remainder of the reducing agent may be added at a later point in the process.

In the preferred embodiment of the present process the order of addition of various ingredients is as follows:

(a) an aldonolactone is dissolved in an organic solvent;

(b) a mixture of an antioxidant and part of a reducing agent is added to the solution obtained in step (a);

(c) an amine is added to the solution obtained in step (b);

(d) the remainder of the reducing agent is added to the solution obtained in step (c).

Typically, the reaction mixture is continuously heated and the various ingredients are added gradually, with stirring, so that the reaction is completed by the time all ingredients are added and dissolved. According to the inventive process the temperature during mixing and reacting is not higher than 65° C., preferably not higher than 55° C.; the reaction time ranges from about 20 minutes to about 60 minutes. Preferably, in order to maximize the yield and minimize the subsequent discoloration the reaction time is from 25 to 35 minutes.

Any N-substituted aldonamide may be synthesized according to the present process, as long as a particular primary or secondary amine $HNR^1R^2$ required to produce that aldonamide is available commercially or can be synthesized.

DETAILED DESCRIPTION OF THE INVENTION

The inventive process is suitable for synthesis of any N-substituted aldonamide. Examples of aldonamides include but are not limited to lactobionamides, gluconamides, maltobionamides, cellobionamides, melibionamides, gentiobionamides and the like.

Starting materials employed in the inventive processes include an aldonolactone, a primary or secondary amine carrying the desired $R^1$ and $R^2$ groups, an organic polar solvent, an antioxidant, and a reducing agent. Any organic polar solvent is suitable, for example aliphatic alcohols, glycols and glycol monoethers, such as methanol, ethanol, isopropanol, ethylene glycol, polyethylene glycol, triethylene glycol, diethylene glycol, diethylene glycol monoethyl ether, ethylene glycol monobutyl ether, ethylene glycol monoethyl ether, ethylene glycol monomethyl ether, diethylene glycol monobutyl ether, and triethylene glycol monomethyl ether. Of course, other polar solvents not listed above may be employed. According to the present invention, in order to maximize color stability, the solvent is selected from the group consisting of methanol, ethanol, isopropanol and acetone.

Aldonolactone is defined as a lactone of an aldonic acid.

Aldonolactones may be obtained commercially, (e.g., from Aldrich Chemicals) or they may be prepared by dissolving an aldonic acid in an organic solvent such as dioxane or methanol. Preparation of aldonolactones is described in a greater detail by Williams et al., "A new Class of Glycolipids: Synthesis, Characterization, and Interaction with Lectins," Archives of Biochemistry and Biophysics, Vol. 195, No. 1, June, 145-151, 1979 and by H. S. Isbell, Bureau of Standards, Journal of Research, Vol. 11, 1933 which disclosures are incorporated by reference herein. Alternatively, aldonolactones may be obtained by spray drying an aqueous solution as described in U.S. Pat. No. 2,746,916, incorporated by reference herein. An aldonolactone preferably employed in the present invention is an aldono-1,5-lactone. Typically, aldonolactones contain some impurities, including the parent reducint saccharide. Although not wishing to be bound by this theory, it is believed that the discoloration of aldonamide may be caused at least in part by Maillard reaction between sugars present in aldonolactones (such as lactose present in aldobiono-1,5-lactone) and amine.

The amine, $HNR^1R^2$, may be obtained commercially (Aldrich Chemicals) as in the case of aliphatic amine, or from Sherex as in the case of alkyloxy alkylamine (e.g., alkyloxypropyl amine [Adogen 180 ®]) or it may be synthesized. When aliphatic amines are employed $R^1$ and/or $R^2$ contain at least 3 carbon atoms to ease synthesis (amines wherein $R^1$ and/or $R^2$ contain fewer than 3 carbon atoms have to be bubbled in due to their high volatility).

According to the inventive process, an antioxidant and a reducing agent am added in order to eliminate or substantially reduce the discoloration or browning of aldonamides during subsequent elevated temperature processing of compositions incorporating the aldonamides. Although some improvement in color and color stability of aldonamides is observed upon the addition of either an antioxidant or a reducing agent, the addition of both an antioxidant and a reducing agent results in synergistic improvement in color and color stability.

According to the present invention, suitable antioxidants include but are not limited to mercaptan or sulfite compounds. Examples of suitable compounds include N-acetyl-L-cysteine, L-cysteine, reduced glutathione, urea, ammonium sulfate ascorbic acid, sodium sulfite, sodium metabisulfite, sodium thiosulfate, furfuryl mercaptan, 2-mercaptoacetic acid, 2-mercaptopropionic acid, 4-mercaptobutyric acid, 1-propanethiol, ethane thiol, 2-mercaptoethanol, iso-amylnitrite, $\beta$-mercapto-DL-isoleuoine, benzoyl peroxide, dimethyl disulfide, diethyl disulfide, benzyl disulfide, thiophenol, p-toluenethiol, O-mercaptobenzoic acid, diphenyldisulfide, or mixtures thereof. Preferred antioxidants are sodium bisulfite, sodium metabisulfite, reduced glutathione, due to their low price and high efficacy. The amount of the antioxidant employed in the inventive process ranges from 0.1% to 2%, by theoretical weight of the product. Preferably from 0.2% to 1%, most preferably from 0.4% to 0.6% is included in the reaction mixture, in order to attain best results with regard to color stability.

According to the present invention, suitable reducing agents include but are not limited to metal hydrides, such as sodium borohydride, lithium aluminum hydride, sodium hydride, and mixtures thereof. Preferred reducing agent is sodium borohydride, due to its low cost and relative ease of handling: sodium borohydride is less moisture-sensitive than other sodium hydrides. The amount of the reducing agent employed in the inventive process ranges from 0.02% to 1% by theoretical weight of the product, preferably from 0.05%, to 0.5%, most preferably from 0.1% to 0.4%, to attain best results with regard to initial color.

According to the present invention, the antioxidant and the reducing agent may be added separately or as a mixture. In the preferred embodiment of the present process the order of addition of various ingredients is as follows:

(a) an aldonolactone is dissolved in an organic solvent;
(b) a mixture of an antioxidant and part of a reducing agent is added to the solution obtained in step (a);
(c) an amine is added to the solution obtained in step (b);
(d) the remainder of the reducing agent is added to the solution obtained in step (c).

According to the preferred embodiment of the invention, from about 20% to about 60%, preferably from about 20% to about 40% of the reducing agent (by weight of the total amount of the reducing agent) is added in step (b); the remainder of the reducing agent is added in step (d).

An example of the reaction employed in the inventive synthesis is as follows:

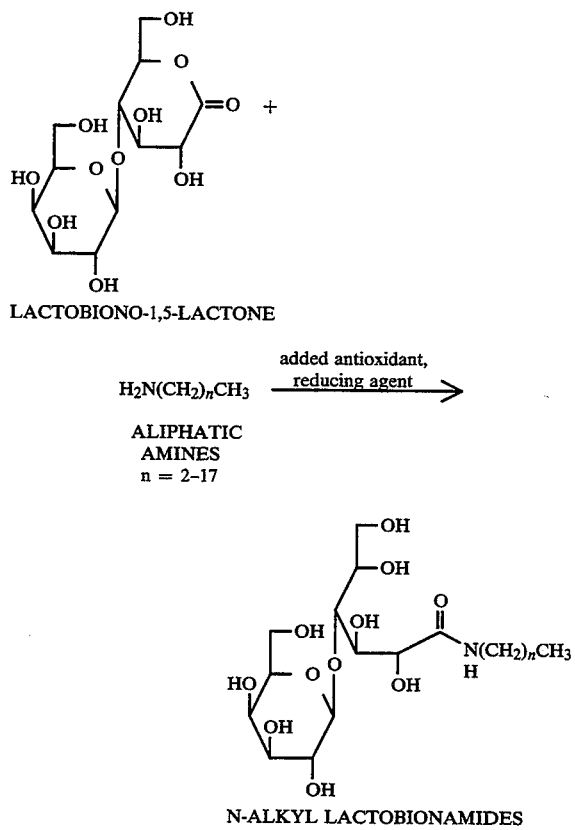

The aldonolactone and the amine constitute 10–50% by weight of the starting reaction mixture, and the solvent constitutes 50–90% by weight. Preferably, the aldonolactone and the amine constitute from about 20% to about 40% of the starting reaction mixture. The molar ratio of the aldonolactone to the amine is in the range of from 1.1:1 to 1:1, preferably in the range of from 1:1 to 1:0.96. Most preferably, the molar ratio of the aldonolactone to the amine in the starting reaction mixture is 1:0.93.

In the first step of the inventive process a homogeneous mixture of starting materials is prepared. Preferably, in order to facilitate the formation of the homogeneous mixture the solvent is slightly heated, typically to a temperature in the range of from 25° to 65° C., preferably in the range of from about 25° C. to 50° C.

It is preferred, in order to optimize purity, that a mixture of the aldonolactone in the solvent is prepared first, with stirring, preferably in a warm solvent. The aldonolactone may be completely dissolved in the solvent, although more frequently only a partial dissolution occurs. The antioxidant, alone or in a mixture with part of the reducing agent is then added gradually, with stirring. The amine, $HNR^1R^2$, is subsequently added, with stirring, preferably gradually or in several portions, in order to attain the homogeneity of the mixture and to optimize the purity of the product. The stirring is conducted with a magnetic stirrer or with an overhead stirrer at moderate rpm. The amine may be added neat (i.e., liquid or melted) or it may be added as a solution in the same solvent that was combined with the aldonolactone. The remainder of the reducing agent (or all of the reducing agent in case none has been added before) is added slowly, with stirring.

The resulting homogeneous mixture is reacted to obtain a reaction product including N-substituted aldonamide. The stirring is typically continued at the same rate as that employed during the mixing step. The reaction may be conducted at room temperature or at an increased temperature. Typically, the reaction temperature is in the range of from about 25° C. to about 65° C., preferably in the range of from about 25° C. to about 50° C., most preferably in the range of from about 25° C. to about 40° C. It is essential to carry out the reaction at a temperature not greater than 65° C. in order to minimize heat decomposition as well as base induced β-elimination. For the same reason, it is important that in the first (mixing) step the temperature does not exceed 65° C. either. Best results are obtained at temperatures not greater than 60° C., most preferably not greater than 50° C.

Typically, the reaction mixture is continuously heated and the various ingredients are added gradually, with stirring, so that the reaction is completed by the time all ingredients are added and dissolved. Thus, steps (i) and (ii) of the inventive process frequently occur simultaneously. According to the present invention, the reaction time ranges from 20 to 60 minutes. Preferably in order to optimize the yield yet to eliminate or minimize subsequent browning, the time ranges from 25 to 35 minutes.

The product, N-substituted aldonamide, may or may not precipitate out of solution. Typically, at least part of N-substituted aldonamide is present in the solution. When the precipitate is formed, it is separated from the solution. The separation may be conveniently carried out by filtering the precipitate out (by gravity or vacuum filtration), although other separation techniques, e.g. centrifugation, may be employed. Preferably, in order to avoid liquid crystal phase formation, additional organic solvent is added to the solution after precipitation of the aldonamide but prior to its separation from the solution. The additional solvent destroys liquid crystal phase, allowing the isolation of the aldonamide as a free-flowing, non-caking solid.

A list of suitable additional organic solvents includes any organic solvent, other than alcohol, e.g., acetone, glycol ethers, such as diethylene glycol monoethyl ether, ethylene glycol monobutyl ether, ethylene glycol monoethyl ether, ethylene glycol monomethyl ether, diethylene glycol monobutyl ether, and triethylene glycol monomethyl ether. Most preferably, the additional solvent is acetone, due to its availability and low toxicity.

The amount of the additional solvent is from 20% to 60%, preferably from 30% to 40% by weight of total reaction mixture.

The product, N-substituted aldonamide is dried. The inventive process typically results in yields of N-substituted aldonamides in the range of from about 80% to about 95%. A further advantage of the inventive process is that the product of improved color and color stability is obtained without the need for washing and recrystallizing the product.

In the inventive process, $R^1$ and $R^2$ groups on the starting amine, $HNR^1R^2$, are attached to the nitrogen of an aldonamide. Thus, depending on the particular amine employed, a variety of N-substituted aldonamides may be synthesized according to the inventive process. Preferably, in order to simplify synthesis and reduce cost, $R^1$ is hydrogen, thus a primary amine is employed. $R^1$ and/or $R^2$ generally contain up to 36 carbon atoms. For the sake of clarity, examples of various substituted aldonamides will be given below using lactobionamide of Formula A, maltobionamide of Formula B and gluconamide of Formula C as an illustration. The corresponding ammonium salts of lactobionamide, maltobionamide and gluconamide are illustrated by Formula D, Formula E, and Formula F, respectively.

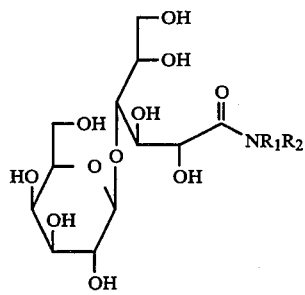

FORMULA A

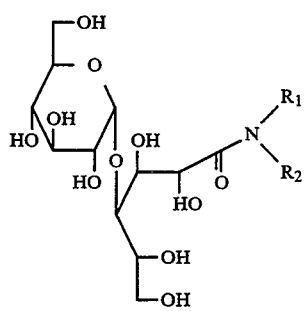

FORMULA B

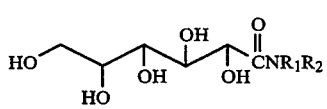

FORMULA C

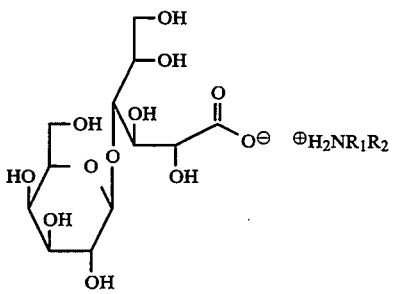

FORMULA D

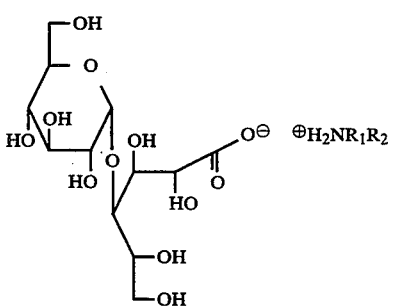

FORMULA E

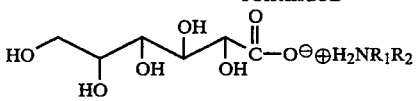

FORMULA F

N-alkyl lactobionamides are compounds of Formula A wherein $R^1$ and/or $R^2$ is an aliphatic hydrocarbon radical (which may include heteroatoms). Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by benzyl, aniline, or substituted benzyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

N-lactobionyl aminoacid esters include but are not limited to esters of those amino acids which naturally occur in proteins, e.g., alanine, valine, glycine, lysine, leucine, arginine, aspartic acid, glutamic add, asparagine, glutamine, threonine, serine, cysteine, histidine, tyrosine, methionine, as well as naturally occurring amino acids which are not found in proteins, such as β-alanine, sarcosine, gamma-aminobutyric acid, ornithene, citrulline, and the like. An example of N-lactobionyl amino acid ester is when in Formula A $R^1$ is hydrogen and $R^2$ is

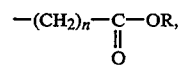

where n is an integer greater than 1 and R is for instance an aliphatic hydrocarbon radical containing up to 36 carbon atoms.

N-(alkyloxy)alkyl lactobionamides are exemplified but not limited to compounds wherein $R^1$ and/or $R^2$ is —$(CH_2)_n$—O—$R^6$, (an ether connected to amine, i.e., an "ether amine" group) wherein n is an integer equal to or greater than 1, preferably from 1 to 10 and $R^6$ is an aliphatic hydrocarbon radical, an aromatic radical, a cydoaliphatic radical as described above for $R^1$ and $R^2$. Preferably n is from 1 to 3 and $R^6$ is an aliphatic hydrocarbon radical containing 1 to 18 carbon atoms.

N-alkyl lactobionamides, N-(alkyloxy)alkyl lactobionamides and N-lactobionyl aminoacid esters typically contain up to 36 carbon atoms in $R^1$ and $R^2$ groups, preferably up to 24 carbon atoms, most preferably from 8 to 18 carbon atoms, and optimally from 10 to 16 carbon atoms in order to attain optimum surface activity.

N-(polyalkyloxy)alkyl lactobionamides are exemplified by but not limited to compounds wherein $R^1$ and/or $R^2$ is —$R^4$—$(OR^4)_n$—$R^4$—$R^5$ wherein n is an integer greater than 1, $R^4$ is selected from the group consisting of ethylene, propylene, and mixtures thereof; and $R^5$ is an amine or lactobionamide moiety. The number of repeating units in the alkylene oxide radical typically ranges from 2 to 10,000, preferably is from 2 to 100, most preferably from 2 to 10. $R^5$ is preferably lactobionamide (the resulting compound is N-(polyalkyloxy)alkyl (bis) lactobionamide) in order to provide an additional β-galactose moiety. R¹ and/or R² groups within N-(polyalkyloxy)alkyl lactobionamides may contain heteroatoms; for instance, R² may be —CH$_2$CH$_2$—S—CH$_2$CH$_2$—(OCH$_2$OCH$_2$)$_n$—S—CH$_2$CH$_2$—R$^5$.

Of course, other R¹ and R² radicals not listed above but within the scope of the claims may be employed.

N-substituted maltobionamides, cellobionamides, melibionamides, gentibionamides and other aldonamides analogous to N-substituted lactobionamides discussed in detail above may be produced according to the present invention, as long as a particular primary or secondary amine, which is necessary to deliver the desired R¹ and/or R² group to the nitrogen atom of the aldonamide is commercially available or can be synthesized.

The following specific examples further illustrate the present invention, but the invention is not limited thereto.

Dodecyl and decylamines (99–96%) were obtained from Aldrich Chemicals and A.C.S. certified grade methanol which contained 0.02–0.1% of water was used.

NaHSO$_3$ was obtained from Fisher Scientific Co.

NaBH$_4$ was obtained from Aldrich Chemicals.

Absorbance measurements were performed by using Hewlett Packard 8450A diode array spectrophotometer, in a cuvette of 1 cm pathlength.

EXAMPLE 1

Synthesis of coco lactobionamide with 0.1% of NaBH$_4$ and 0.4% of NaHSO$_3$

Lactobiono-1,5-lactone (150 g, 1 eq) was dissolved in warm methanol (465 ml, 50 C.) with sufficient stirring. NaHSO$_3$ (0.92 g) (0.4% by theoretical weight of coco lactobionamide) was added followed by gradual addition of coco amine (82 g, 1 eq). Subsequently, 0.23 g of NaBH$_4$ (0.1% by theoretical weight of coco lactobionamide) was added slowly. The reaction was stirred at 50° C. for 15 minutes. The solution was cooled to room temperature. After precipitation occurred, 700 ml of acetone was added slowly. The reaction was filtered and dried in vaccum oven at 40° C. The initial yield was ~90%. The absorbances of the filtrate and of the 10% aqueous solution of the lactobionamide were measured.

|  | Absorbance 400 nm |
|---|---|
| Filtrate | 0.063 |
| 10% Aqueous solution | 0.0458 |

10% aqueous solution of coco lactobionamide was stored at 85° C. for 1½ hours. The absorbance of this solution at 400 nm, after storage, was 0.1487.

EXAMPLE 2

Synthesis of coco lactobionamide with 0.4% of NaBH$_4$ and 0.6% of NaHSO$_3$

Lactobiono-1,5-latone (150, 1 eq) was dissolved in warm methanol (465 ml, 50° C.) with sufficient stirring, a mixture containing 1.32 g of NaHSO$_3$ (0.6% by the theoretical weight of coco lactobionamide) and 0.29 g of NaBH$_4$ (31% of total NaBH$_4$) was added followed by a gradual addition of coco amine(82 g,0.95 eq). Subsequently, the remaining 0.63 g of NaBH$_4$ was added slowly follow by stirring at 50° C. for 15 minutes. The reaction was cooled to room temperature followed by addition of 700 ml acetone. The product was filtered and dried in vaccum oven at 40° C. The absorbances of filtrate and of 10% aqueous solution of coco lactobionamide were measured:

|  | Absorbence 400 nm |
|---|---|
| Filtrate | 0.036 |
| 10% Aqueous Solution | 0.0321 |

10% aqueous solution of coco lactobionamide was stored at 85° C. for 1½ hours. The absorbance of this solution at 400 nm, after storage was 0.085.

This example when compared with Example 1, demonstrates that improved color and color stability (lower absorbance values) are obtained in accordance with the preferred process of the invention, wherein part of a reducing agent is added in a mixture with an antioxidant and the remainder of the reducing agent is added after the addition of the amine.

EXAMPLE 3

Synthesis of Tallow lactobonamide with 0.4% of NaBH$_4$ and 0.6% of NaHSO$_3$

A procedure described in Example 2 was employed, except that tallow amine (Adogen ® 170-D from Sherex) was used instead of coco amine. The solid product and filtrate were colorless. Filtrate absorbance at 400 nm was 0.0363.

EXAMPLE 4

Synthesis of dodecyl lactobionamide with 0.4% of NaBH$_4$ and 0.6% of NaHSO$_3$

A procedure described in Example 2 was employed, except that dodecyl amine was used instead of coco amine. The yield was 92%. Absorbances of the filtrate and of 10% aqueous solution of dodecyl lactobionamide were measured.

|  | Absorbence 400 nm |
|---|---|
| Filtrate | 0.0511 |
| 10% Aqueous Solution | 0.0382 |

EXAMPLE 5

Synthesis of decyl lactobionamide with 0.4% of NaBH$_4$ and 0.6% of NaHSO$_3$

A procedure described in Example 2 was employed, except that decyl amine was used instead of coco amine. The yield was 90%. The absorbances of the filtrate and of the 10% aqueous solution of decyl lactobionamide were measured.

|  | Absorbance 400 nm |
|---|---|
| Filtrate | 0.0621 |
| 10% Aqueous Solution | 0.0334 |

Comparative Examples

EXAMPLE 6

Synthesis of coco lactobionamide with 2% of NaHSO$_3$

Lactobiono-1,5-lactone (340 g, 1 eq) was dissolved in 800 ml of warm methanol (50° C.). 8.4 g of NaHSO$_3$ (2% by theoretical weight of coco lactobionamide) were added followed by addition of 194 g of coco amine and stirred for 15 minutes. 1200 ml of acetone were added after precipitation occurred. The solid was filtered, the filtrate had a light yellowish color. The solid (coco lactobionamide) after drying had a slightly off-white color even though high concentration of NaHSO$_3$ was employed. The color of the filtrate turned slightly more yellowish after storage for 48 hours. The absorbance of the 10% aqueous solution of coco lactobionamide at 400 nm was 0.0498, which was higher than 0.0458 and 0.0321 values obtained in Examples 1 and 2. Thus, improved color was attained in Examples 1 and 2, compared to Example 6, due to the inclusion of a reducing agent in Examples 1 and 2. 10% aqueous solution of coco lactobionamide was stored at 85° C. for 1½ hours. The absorbance of this solution at 400 nm, after storage was 0.0784. This absorbance was lower than in Examples 1 and 2 (after storage) due to a large amount of NaHSO$_3$ used since NaHSO$_3$ is a main contributor to color stability improvement.

This example, when compared with Examples 1 and 2, demonstrates that the inclusion of a reducing agent in a reaction mixture is critical for attaining an aldonamide having improved color and color stability.

EXAMPLE 7

Synthesis of Coco Lactobionamide (No Additives)

A procedure identical to Example 6 was employed except that no NaHSO$_3$ was added. The filtrate had brown color and the solid (coco lactobionamide) turned brownish at the surfaces after drying at 50° C. for several hours. The filtrate turned dark brown after storage for 24 hours.

|  | Absorbence 400 nm |
|---|---|
| Filtrate | 0.0765 |
| 10% aqueous solution | 0.19 |

10% aqueous solution of coco lactobionamide was stored at 85° C. for 1½ hours. The absorbance of this solution at 400 nm, after storage was 0.290.

This Example, when compared with Examples 1, 2, and 6, demonstrates that the inclusion of both an antioxidant and a reducing agent results in improved color and improved color stability of the aldonamides.

EXAMPLE 8

Synthesis of dodecyl lactobionamide with 0.4% of NaBH$_4$

A procedure identical to Example 6 was employed except that 0.4% NaBH$_4$ was used instead of HaHSO$_3$, and dodecyl amine was used instead of coco amine.

The filtrate had a light yellowish color. The solid had an off-white color. The filtrate turned yellowish after storage for 48 hours.

This Example, when compared with Example 4, demonstrates that the presence of the antioxidant, in addition to the reducing agent, is critical for attaining aldonamides of improved color and improved color stability.

Table I summarizes results obtained in the examples.

TABLE I
EXAMPLE SUMMARY

| | | | | ABSORBANCE | |
|---|---|---|---|---|---|
| Example | Additives | Product | Filtrate | 10% Aqueous Solution of the Product (% Improvement Compared to Example 7) | 10% Aqueous Solution of the Product After Storage (% Improvement Compared to Example 7) |
| 1 | 0.1% NABH$_4$/ 0.4% NaHSO$_3$ | coco lactobionamide | 0.063 | 0.0458 (76%) | 0.1487 (49%) |
| 2 | 0.4% NaBH$_4$/ 0.6% NaHSO$_3$ | coco lactobionamide | 0.036 | 0.0321 (83%) | 0.085 (71%) |
| 3 | 0.4% NaBH$_4$/ 0.6% NaHSO$_3$ | tallow lactobionamide | 0.0363 | | |
| 4 | 0.4% NABH$_4$/ 0.6% NaHSO$_3$ | dodecyl lactobionamide | 0.0511 | 0.0382 | |
| 5 | 0.4% NaBH$_4$/ 0.6% NAHSO$_3$ | decyl lactobionamide | 0.0621 | 0.0334 | |
| 6 | 2% NaHSO$_3$ | coco lactobionamide | | 0.0498 (74%) | 0.0784 (73%) |
| 7 | None | coco lactobionamide | 0.0765 | 0.19 | 0.290 |
| 8 | 0.4% NABH$_4$ | dodecyl lactobionamide | | | |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A process of preparing an N-substituted aldonamide, the process comprising the steps of:

i) preparing a homogeneous mixture comprising an aldonolactone, a reducing agent, an antioxidant, an organic polar solvent, and an amine $HNR^1R^2$, wherein $R^1$ and $R^2$ are the same or different and may contain heteroatoms and are selected from the group consisting of hydrogen, an aliphatic hydrocarbon radical, an aromatic radical, a cycloaliphatic radical, an amino acid ester, an ether amine and mixtures thereof selected from the group consisting of oxygen, nitrogen and sulphur, except that $R^1$ and $R^2$ are not both hydrogen at the same time, wherein the molar ratio of the aldonolactone to the amine is in the range of from about 1.1:1 to about 1:1; and ii) reacting the homogeneous mixture at a temperature not greater than 65° C. to obtain the aldonamide.

2. The process of claim 1 further comprising separating the aldonamide from the solution obtained in step (ii).

3. The process of claim 2 further comprising adding an additional solvent to the solution obtained in step (ii) prior to separating the aldonamide.

4. The process of claim 3 wherein the additional solvent is an organic solvent other than an alcohol.

5. The process of claim 4 wherein the additional solvent is selected from the group consisting of acetone and glycol ethers.

6. The process of claim 1 wherein the antioxidant is selected from the group consisting of N-acetyl-L-cysteine, L-cysteine, reduced glutathione, urea, ammonium sulfate ascorbic acid, sodium bisulfite, sodium metabisulfite, sodium thiosulfate, furfuryl mercaptan, 2-mercaptoacetic acid, 2-mercaptopropionic acid, 4-mercaptobutyric acid, 1-propanethiol, ethane thiol, 2-mercaptoethanol, iso-amylnitrite, β-mercapto-DL-isoleuoine, benyoyl peroxide, dimethyl disulfide, diethyl disulfide, benzyl disulfide, thiophenol, p-toluenethiol, O-mercaptobenzoic acid, diphenyldisulfide, and mixtures thereof.

7. The process of claim 6 wherein the antioxidant is selected from the group consisting of sodium bisulfite, sodium metabisulfite, and mixtures thereof.

8. The process of claim 1 wherein the reducing agent is a metal hydride.

9. The process of claim 1 wherein the amount of the reducing agent is from 0.02% to 1% by theoretical weight of the product.

10. The process of claim 1 wherein the amount of the antioxidant is from 0.1% to 2% by theoretical weight of the product.

11. The process of claim 1 wherein step (i) of the process comprises dissolving the aldonolactone in the organic polar solvent, adding the antioxidant, adding the amine, and adding the reducing agent.

12. The process of claim 1 wherein step (i) of the process comprises dissolving the aldonolactone in the organic polar solvent, adding a mixture of the antioxidant and part of the reducing agent, adding the amine, and adding the remainder of the reducing agent.

13. The process of claim 1 wherein from about 20% to about 50% of the reducing agent is added in the mixture with the antioxidant.

14. The process of claim 1 wherein the mixing is conducted at a temperature in the range of from 25° C. to 65° C.

15. The process of claim 1 wherein the aldonolactone is an aldono-1,5-lactone.

16. The process of claim 1 wherein the reaction in step (ii) is conducted at a temperature in the range of 25° to 65° C.

17. The process of claim 1 wherein the reaction in step (ii) is conducted at a temperature not greater than 50° C.

18. The process of claim 1 wherein $R^1$ is hydrogen.

19. The process of claim 1 wherein the aldonamide is selected from the group consisting of lactobionamides, gluconamides, maltobionamides, cellobionamides, melibionamides, and gentiobionamides.

20. The process of claim 1 wherein $R^1$ and $R^2$ are the same or different and both together include from 1 to 36 carbon atoms.

21. The process of claim 1 wherein step (i) and step (ii) are conducted for a total time period of from 20 minutes to 60 minutes.

* * * * *